United States Patent
Howie (10) Patent No.: US 10,444,132 B2
(45) Date of Patent: Oct. 15, 2019

(54) MOBILE BIPENDULUM IMPACT TEST MACHINE

(71) Applicant: Bell Helicopter Textron Inc., Fort Worth, TX (US)

(72) Inventor: Kevin Thomas Howie, Lewisville, TX (US)

(73) Assignee: Bell Helicopter Textron Inc., Fort Worth, TX (US)

( * ) Notice: Subject to any disclaimer, the term of this patent is extended or adjusted under 35 U.S.C. 154(b) by 344 days.

(21) Appl. No.: 15/639,655

(22) Filed: Jun. 30, 2017

(65) Prior Publication Data

US 2019/0003942 A1 Jan. 3, 2019

(51) Int. Cl.
   *G01N 3/48* (2006.01)
   *G01N 3/303* (2006.01)

(52) U.S. Cl.
   CPC ..... *G01N 3/303* (2013.01); *G01N 2203/0073* (2013.01); *G01N 2203/0206* (2013.01)

(58) Field of Classification Search
   USPC .......................................... 73/12.14, 81, 82
   See application file for complete search history.

(56) References Cited

U.S. PATENT DOCUMENTS

| | | | | |
|---|---|---|---|---|
| 5,003,811 A | * | 4/1991 | Shannon | G01N 3/30 73/12.14 |
| 2004/0103713 A1 | * | 6/2004 | Voon | G01N 3/48 73/12.04 |
| 2015/0052972 A1 | * | 2/2015 | Ruth | G01N 3/303 73/12.14 |
| 2018/0172551 A1 | * | 6/2018 | Pradeep | G01M 7/08 |

OTHER PUBLICATIONS

"A convenient world first", NLR 2013 online annual report p. 12 (retrieved from http://annualreport.nir.nl/2013/NLR%20Projects/Competitveness/Portable%impactor/), 2013.
"Pendulum Impact Test Systems", date unknown (retrieved Jun. 28, 2017 from https://www.mts.com/en/products/producttype/test-systems/load-frames-uniaxial/universal/Impact/index.htm).

* cited by examiner

*Primary Examiner* — Robert R Raevis
(74) *Attorney, Agent, or Firm* — Winstead PC (57) ABSTRACT

A bipendulum impact test machine for imparting impact damage includes a frame of beams where a weighted sled swings from a pair of links extending from a carriage. The carriage and sled are vertically adjustable along a set of vertical shafts of the frame. The sled is permanently horizontally oriented and parallel with the carriage. Interchangeable impact tips are removably and adjustably engaged with the sled. The impact tips have a variety of shapes in order to simulate different impact scenarios. The device is mobile and capable of imparting impact damage to large aircraft parts even in an installed condition.

20 Claims, 7 Drawing Sheets

MOBILE BIPENDULUM IMPACT TEST MACHINE

BACKGROUND

This section provides background information to facilitate a better understanding of the various aspects of the disclosure. It should be understood that the statements in this section of this document are to be read in this light, and not as admissions of prior art.

Pursuant to Title 14 of the Code of Federal Regulations § 29.573 regarding certification of aircraft using composite structures, critical components must be fatigue tested with previously inflicted flaws to account for a worst-case condition. Impact damage is one type of flaw required in test components to simulate real world impacts during the manufacturing and operational phases of aircraft life. Prior art impact testing machines include vertical drop towers and spring loaded impact guns. Vertical drop towers are bulky, difficult to position, and because of freefalling impactors provide inexact point and shape of impact. Vertical drop towers cannot be used when a horizontal impacting direction is required. Spring loaded impact guns have difficulty with containment of the reaction force as well as double impact issues. Prior pendulum type impactors are typically used for Charpy and Izod small coupon fatigue testing, are ineffective for imparting impact damage on large aircraft components, and cannot be manipulated to specific locations on the large airframe structures.

SUMMARY

An example of a mobile impact test machine includes a set of parallel and coplanar vertical shafts connected to a frame, a threaded rod operatively engaged with the frame, a carriage supported by the threaded rod and slidingly engaged with the set of vertical shafts, a first link pivotally engaged with the carriage and pivotally engaged with a sled, a second link parallel with the first link and pivotally engaged with the carriage and with the sled, and an impact tip removably attached to the sled.

An example of a repositionable impact test machine for imparting impact damage on a test specimen includes a baseplate and a canopy connected to a set of beams, a first vertical shaft connected to the baseplate and the canopy, a second vertical shaft parallel and coplanar with the first vertical shaft connected to the baseplate and the canopy, a threaded rod threadably engaged with the canopy, a carriage supported by the threaded rod and slidingly engaged with the first vertical shaft and the second vertical shaft, a first link pivotally engaged with the carriage and pivotally engaged with a sled, a second link parallel with the first link pivotally engaged with the carriage and pivotally engaged with the sled, an impact tip removably attached to the sled, wherein the sled moves between a raised position and an impact position, and wherein the impact tip is configured to be tangent the test specimen at the impact position.

An example of a method for imparting impact damage to a test specimen through an impact tip pivotally attached by a set of links to an adjustable carriage, wherein the impact tip has a raised position and an impact position including positioning the impact tip adjacent the test specimen, placing the impact tip at the raised position to achieve a desired impact force of the impact tip against the test specimen, releasably securing the impact tip at the raised position, releasing the impact tip such that the impact tip pivots about the set of links to the impact position, and impacting the test specimen with the impact tip.

This summary is provided to introduce a selection of concepts that are further described below in the detailed description. This summary is not intended to identify key or essential features of the claimed subject matter, nor is it intended to be used as an aid in limiting the scope of claimed subject matter.

BRIEF DESCRIPTION OF THE DRAWINGS

The disclosure is best understood from the following detailed description when read with the accompanying figures. It is emphasized that, in accordance with standard practice in the industry, various features are not drawn to scale. In fact, the dimensions of various features may be arbitrarily increased or reduced for clarity of discussion.

DETAILED DESCRIPTION

It is to be understood that the following disclosure provides many different embodiments, or examples, for implementing different features of various embodiments. Specific examples of components and arrangements are described below to simplify the disclosure. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed.

Figure 1:
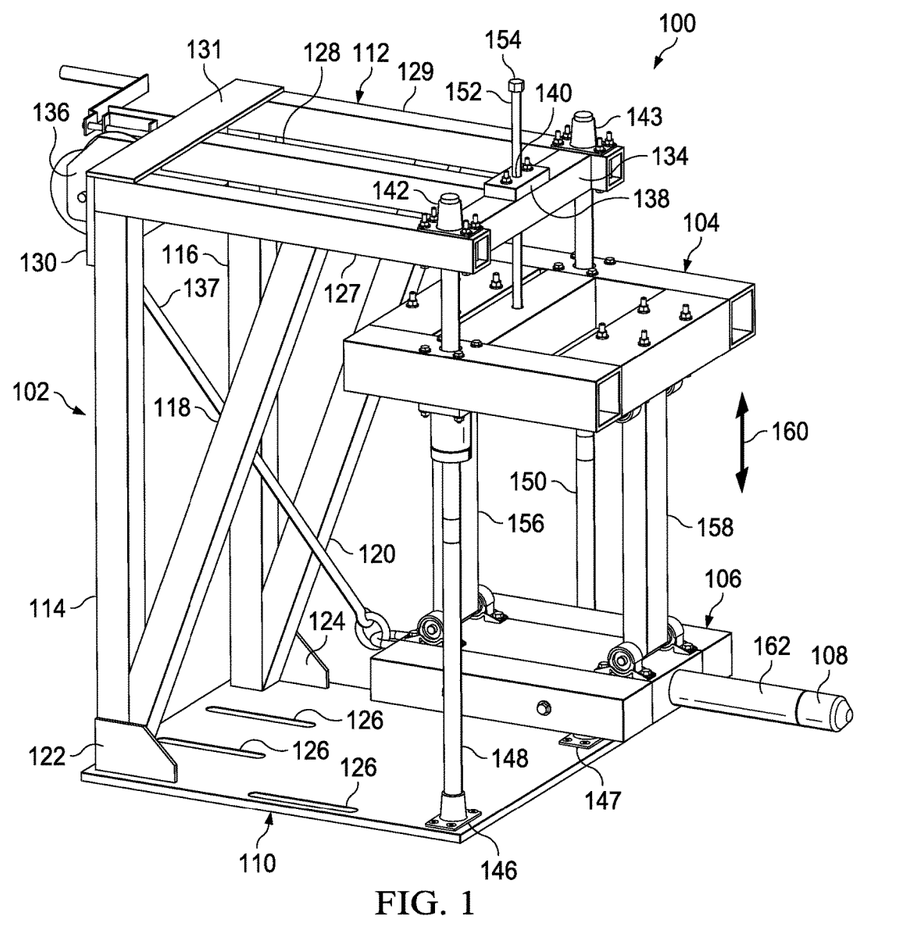
FIG. 1 is a perspective view of a bipendulum impact device according to an exemplary embodiment.

Referring to FIG. 1, an exemplary bipendulum impact device 100 is shown. Impact device 100 includes frame 102, carriage 104, sled 106, and impact tip 108. Frame 102 includes baseplate 110 spaced from canopy 112. Baseplate 110 is generally planar and includes mounting slots 126. An exemplary baseplate 110 may be constructed of 0.5 inch aluminum plate and can range in thickness from 0.25 to 1 inch and be constructed of other materials such as steel plate or high-density polyethylene/polyvinyl plastic. Vertical beams 114 and 116 are attached to and extend from baseplate 110 in adjacent corners. Vertical beams 114 and 116 are attached to canopy 112. Brace 118 is attached to vertical beam 114 and baseplate 110 with gusset 122. Brace 120 is attached to vertical beam 116 and baseplate 110 with gusset 124. Braces 118 and 120 extend angularly from baseplate 110 and are attached to canopy 112. Exemplary vertical beams and braces may be constructed of two inch square aluminum tubing and can range from one to three inch square or rectangular tubing constructed of other materials such as stainless steel or high-density polyethylene/polyvinyl plastic tubing.

Canopy 112 includes beams 127, 128, and 129 attached to and extending from plates 130 and 131. Canopy 112 is generally vertically aligned with baseplate 110. Exemplary beams may be constructed of two inch square aluminum tubing and can range from one to three inch square or rectangular tubing constructed of other materials such as stainless steel or high-density polyethylene/polyvinyl plastic tubing. Exemplary plates 130 and 131 may be constructed of 0.5 inch aluminum plate and can range in thickness from 0.25 to 0.75 inch and be constructed of other materials such as steel plate or high-density polyethylene/polyvinyl plastic. Winch 136 is attached to plate 130. Strap 137 is releasably connected between sled 106 and winch 136 with a quick release clasp. Beams 127, 128, and 129 are attached to crossbeam 134. Plate 138 is mounted to crossbeam 134. Plate 138 includes threaded hole 140. An exemplary plate 138 may be constructed of 0.75 inch steel plate and can range in thickness from 0.5 to 1 inch and be constructed of other materials such as aluminum or stainless steel plate. Collars 142 and 143 are mounted to beams 127 and 129, respectively. Collars 146 and 147 are mounted to baseplate 110 in adjacent corners. Collar 142 is axially aligned with collar 146. Collar 143 is axially aligned with collar 147. Collars 142, 143, 146, and 147 are sized to receive and secure vertical shafts 148 and 150. Vertical shafts 148 and 150 extend between baseplate 110 and canopy 112. Vertical shafts 148 and 150 are generally parallel and coplanar. An exemplary vertical shaft may be constructed of one inch diameter polished steel and can range in diameter from 0.5 to 1.5 inch and be constructed of other materials such as aluminum or plastic.

Threaded rod 152 passes through and is rotatable within crossbeam 134 and carriage 104. Threaded rod 152 includes threads sized to engage threaded hole 140. Threaded rod 152 includes tool head 154 on one end for engagement with a torque producing tool and a nut/washer combination on an opposite end to support carriage 104 while allowing rotation of threaded rod 152 relative to crossbeam 134. Rotation of threaded rod 152 adjusts the vertical position of impact tip 108 in direction 160 relative to frame 102. Rotation of threaded rod 152 moves carriage 104, links 156 and 158, and sled 106 simultaneously along vertical shafts 148 and 150. An exemplary threaded rod may be constructed of 0.5 inch diameter steel and can range in diameter from 0.25 to 0.75 inch.

Links 156 and 158 are pivotally attached to carriage 104. Links 156 and 158 are pivotally attached to sled 106. The pivotal connections provided by the links allow the sled to swing relative to the carriage between an impact position and a raised position. Links 156 are 158 have identical dimensions and ensure that sled 106 is always held in a generally horizontal position parallel with carriage 104 and baseplate 110. Impact tip 108 is interchangeably attached to sled 106. An exemplary impact tip 108 is interchangeably attached to extender 162 and extender 162 is removably attached to sled 106.

Figure 2A:
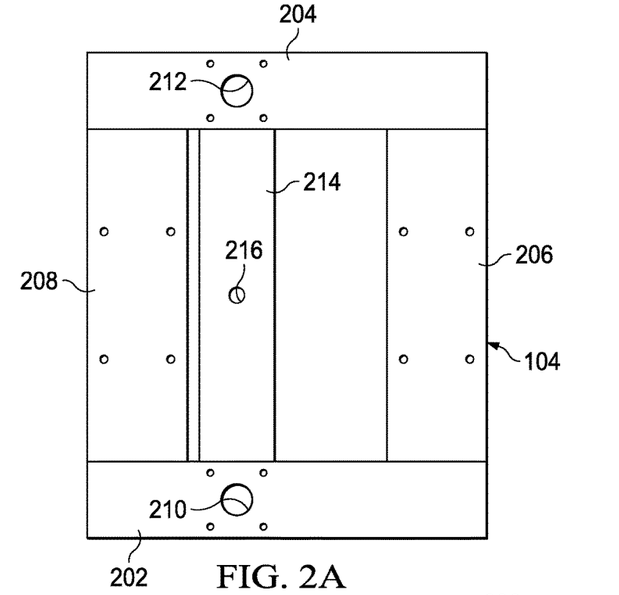
FIG. 2A is a top view of a carriage according to an exemplary embodiment.
Figure 2B:
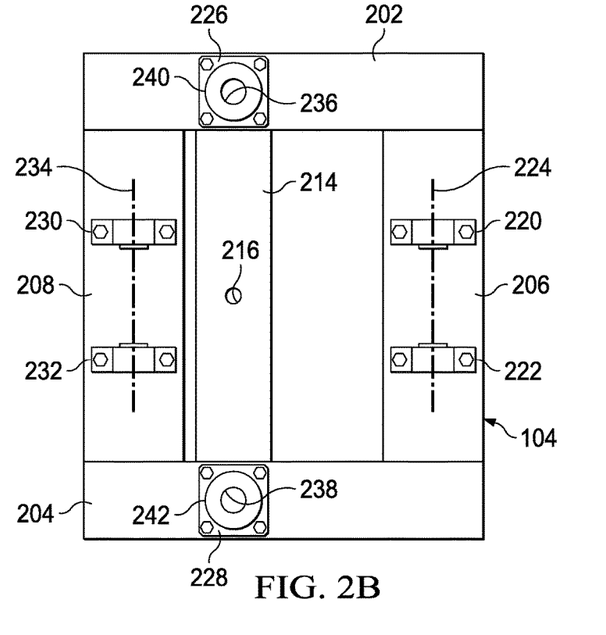
FIG. 2B is a bottom view of a carriage according to an exemplary embodiment.

Referring to FIGS. 2A and 2B, carriage 104 is shown. Carriage 104 includes side beams 202 and 204 connected to crossbeams 206 and 208. Exemplary side beams and crossbeams may be constructed of two inch square aluminum tubing and can range from one to three inch square or rectangular tubing constructed of other materials such as stainless steel or high-density polyethylene/polyvinyl plastic. Side beam 202 includes hole 210. Side beam 204 includes hole 212. Holes 210 and 212 are sized to slidingly receive vertical shafts 148 and 150, respectively. Holes 210 and 212 are oversized clearance holes with respect to the diameter of vertical shafts 148 and 150. Holes 210 and 212 do not encumber horizontal movement of sled 104 with respect to vertical shafts 148 and 150. Center beam 214 is connected to side beam 202 and side beam 204. Center beam 214 includes hole 216. Hole 216 is located generally at the midpoint of center beam 214 and is sized to receive threaded rod 152. Hole 216 is an oversized clearance hole with respect to the diameter of threaded rod 152. Threaded rod 152 is free to rotate with respect to hole 216. Holes 210, 212, and 216 are linearly aligned.

Ball bearings 220 and 222 are mounted to crossbeam 206. Ball bearings 220 and 222 are axially aligned on axis 224. Ball bearings 230 and 232 are mounted to crossbeam 208. Ball bearings 230 and 232 are axially aligned on axis 234.

Linear sleeve bearing 226 is mounted to side beam 202. Linear sleeve bearing 226 includes hole 236 and clamp-on collar 240. Hole 236 is sized to slidingly receive vertical shaft 148. When engaged, clamp-on collar 240 supports linear sleeve bearing 226 and prevents linear sleeve bearing 226 and the carriage from movement along vertical shaft 148. When clamp-on collar 240 is disengaged, linear sleeve bearing 226 is free to slide along vertical shaft 148. Linear sleeve bearing 228 is mounted to side beam 204. Linear sleeve bearing 228 includes hole 238 and clamp-on collar 242. Hole 238 is sized to slidingly receive vertical shaft 150. When engaged, clamp-on collar 242 supports linear sleeve bearing 228 and prevents linear sleeve bearing 228 and the carriage from movement along vertical shaft 150. When clamp-on collar 242 is disengaged, linear sleeve bearing 228 is free to slide along vertical shaft 150.

Figure 3A:
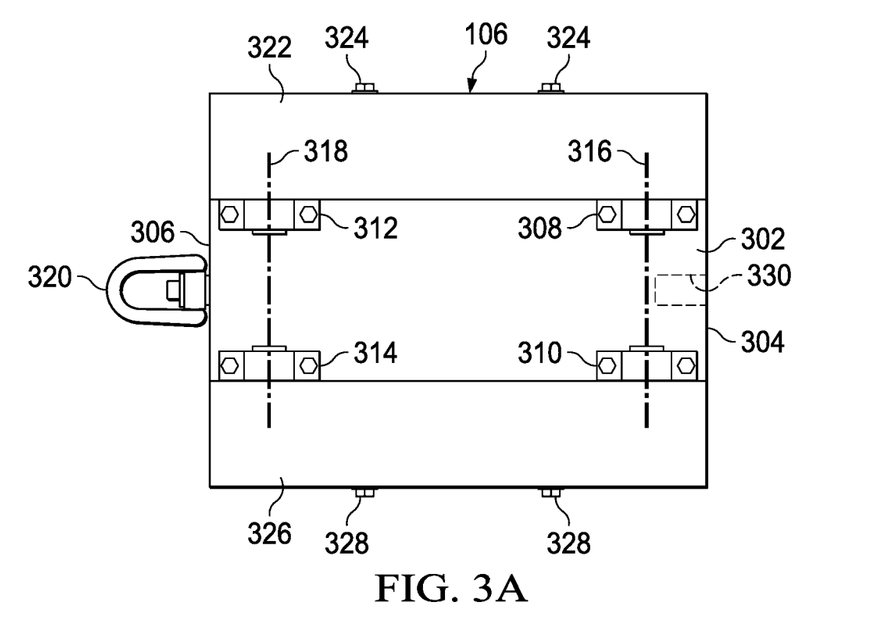
FIG. 3A is a top view of a sled according to an exemplary embodiment.
Figure 3B:
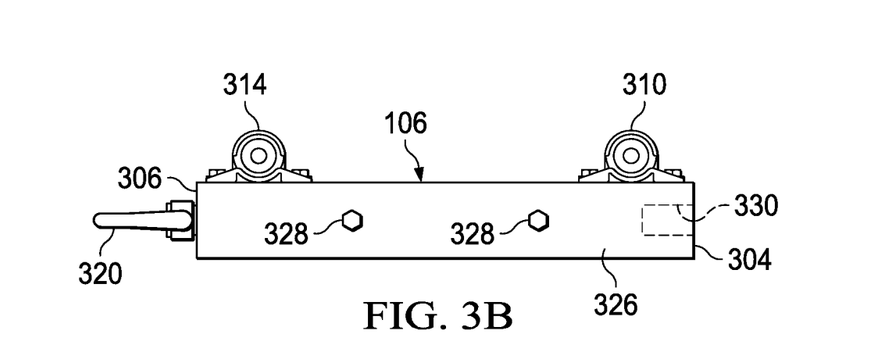
FIG. 3B is a side view of a sled according to an exemplary embodiment.
Figure 4A:
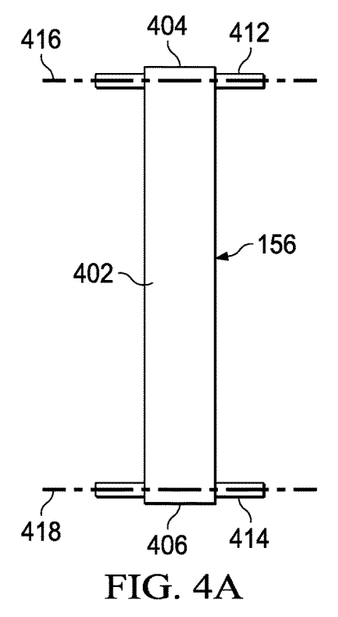
FIG. 4A is a front view of a link according to an exemplary embodiment.
Figure 4B:
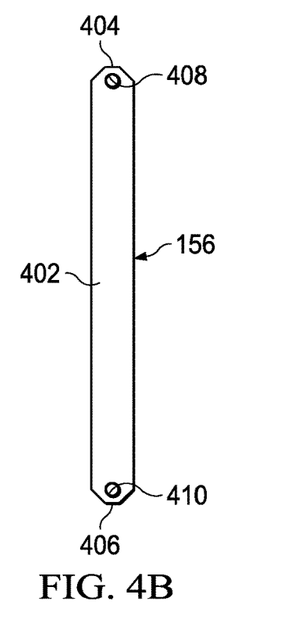
FIG. 4B is a side view of a link according to an exemplary embodiment.
Figure 4C:
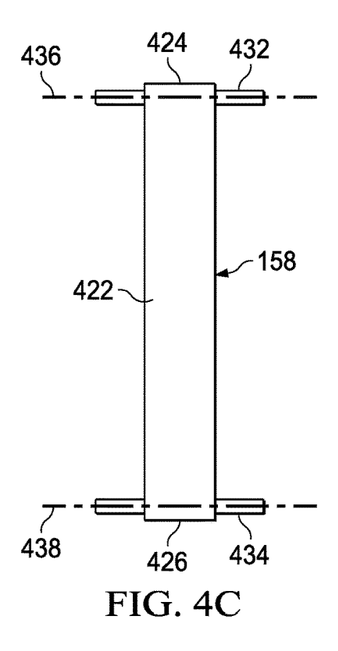
FIG. 4C is a front view of a link according to an exemplary embodiment.
Figure 4D:
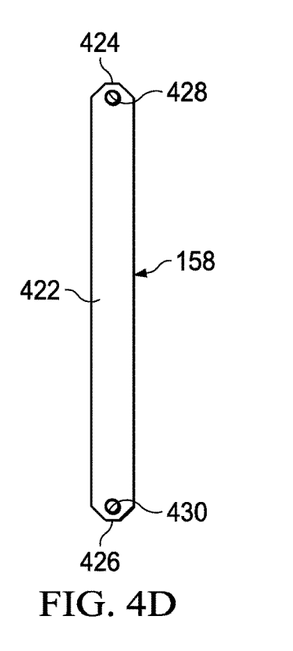
FIG. 4D is a side view of a link according to an exemplary embodiment.

Referring to FIGS. 3A and 3B, sled 106 is shown. Sled 106 includes body 302 having ends 304 and 306. Exemplary sled may be constructed of 2.5 inch thick steel plate and can range from one to four inch thick steel plate or constructed of other materials such as stainless steel or aluminum. Ball bearings 308 and 310 are mounted to body 302 proximate end 304. Ball bearings 308 and 310 are axially aligned on axis 316. Ball bearings 312 and 314 are mounted to body 302 proximate end 306. Ball bearings 312 and 314 are axially aligned on axis 318. Hoist ring 320 is attached to body 302 at end 306. Weight 322 is removably mounted to body 302 with mounting hardware 324. Weight 326 is removably mounted to body 302 with mounting hardware 328. An exemplary sled 106 does not include weights 322 or 326 mounted to body 302. Threaded hole 330 is tapped into body 302 at end 304.

Referring to FIGS. 4A-4D, links 156 and 158 are shown. Link 156 includes body 402 having ends 404 and 406. Body 402 includes hole 408 proximate end 404. Axle 412 is fixed in hole 408. Axle 412 is cylindrical and sized to engage ball bearings 230 and 232. Axle 412 has longitudinal axis 416. Axis 416 is collinear with axis 234 and provides a rotational axis for link 156 with respect to carriage 104. Body 402 includes hole 410 proximate end 406. Axle 414 is fixed in hole 410. Axle 414 is cylindrical and sized to engage ball bearings 312 and 314. Axle 414 has longitudinal axis 418. Axis 418 is collinear with axis 318 and provides a rotational axis for link 156 with respect to sled 106.

Similarly, Link 158 includes body 422 having ends 424 and 426. Body 422 includes hole 428 proximate end 424. Axle 432 is fixed in hole 428. Axle 432 is cylindrical and sized to engage ball bearings 220 and 222. Axle 432 has longitudinal axis 436. Axis 436 is collinear with axis 224 and provides a rotational axis for link 158 with respect to carriage 104. Body 422 includes hole 430 proximate end 426. Axle 434 is fixed in hole 430. Axle 434 is cylindrical and sized to engage ball bearings 308 and 310. Axle 434 has longitudinal axis 438. Axis 438 is collinear with axis 316 and provides a rotational axis for link 158 with respect to sled 106.

Figure 5A:
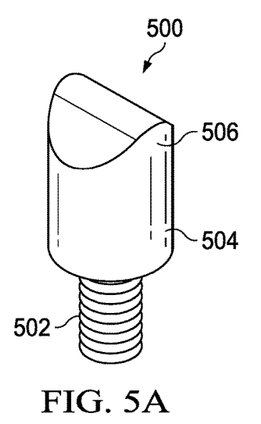
FIG. 5A is a perspective view of an impact tip according to an exemplary embodiment.
Figure 5B:
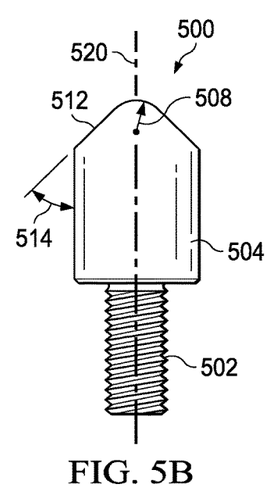
FIG. 5B is a side view of an impact tip according to an exemplary embodiment.
Figure 5C:
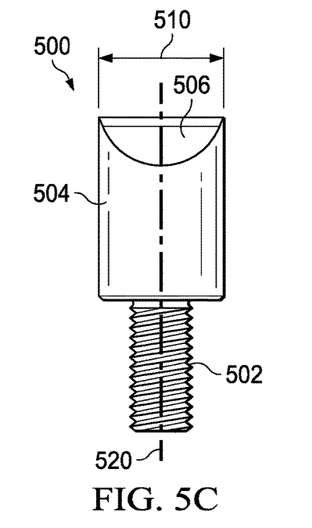
FIG. 5C is an alternate side view of an impact tip according to an exemplary embodiment.

Referring to FIGS. 5A-5C, impact tip 500 is shown. Impact tip 500 is an exemplary cylindrical impact tip. Impact tip 500 includes threaded shaft 502 integrally formed with body 504 having central longitudinal axis 520. Threaded shaft 502 is sized to engage threaded hole 330 or if present, extender 162. Body 504 includes contact area 506. Contact area 506 is cylindrical shaped having radius 508 and length 510. An exemplary radius 508 may be 0.25 to two inches. An exemplary length 510 may be one to three inches. Depending on radius 508, contact area 506 may include transition area 512. Transition area 512 forms angle 514 with body 504. An exemplary angle may range between 30° and 60°. Impact tip 500 imparts linear impact damage intended for impacts on edges and curved surfaces. An exemplary impact tip 500 may be constructed of solid steel or other materials such as stainless steel or high-density polyethylene/polyvinyl plastic.

Figure 6A:
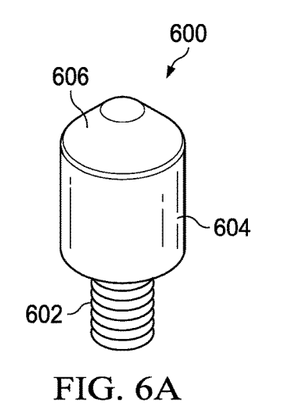
FIG. 6A is a perspective view of an impact tip according to an exemplary embodiment.
Figure 6B:
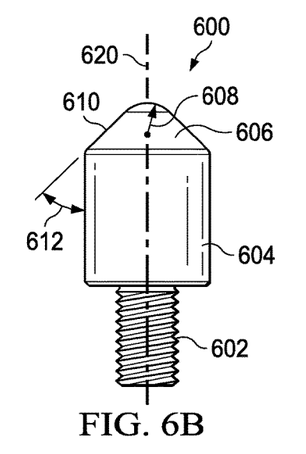
FIG. 6B is a side view of an impact tip according to an exemplary embodiment.

Referring to FIGS. 6A and 6B, impact tip 600 is shown. Impact tip 600 is an exemplary spherical impact tip. Impact tip 600 includes threaded shaft 602 integrally formed with body 604 having central longitudinal axis 620. Threaded shaft 602 is sized to engage threaded hole 330 or if present, extender 162. Body 604 includes contact area 606. Contact area 606 is spherical shaped having radius 608. An exemplary radius 608 may be 0.25 to two inches. Depending on radius 608, contact area 606 may include transition area 610. Transition area 610 forms angle 612 with body 604. An exemplary angle may range between 30° and 60°. Impact tip 600 imparts spherical impact damage intended for impacts on generally flat surfaces. An exemplary impact tip 600 may be constructed of solid steel or other materials such as stainless steel or high-density polyethylene/polyvinyl plastic.

Figure 7:
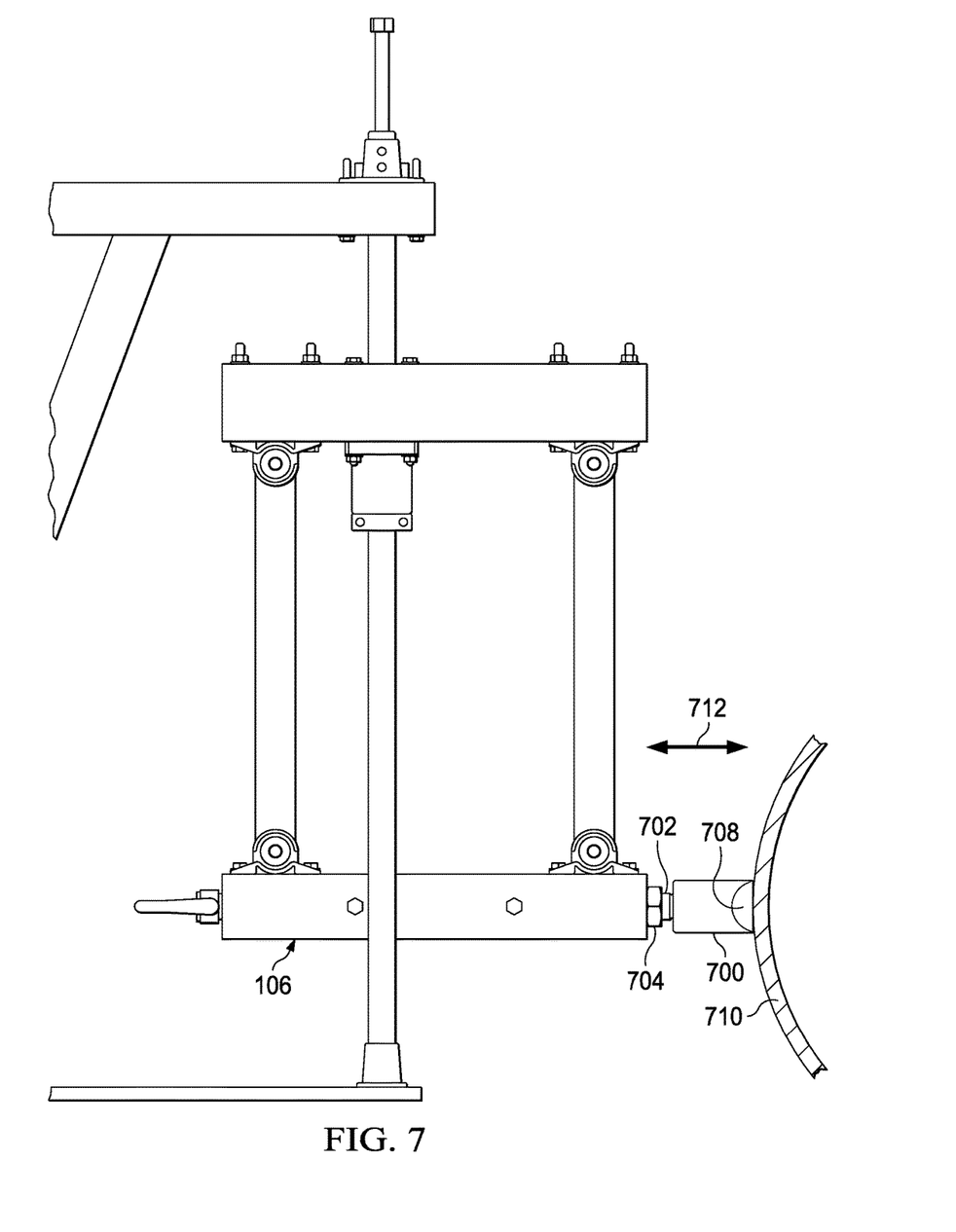
FIG. 7 is a partial side view of an impact tip connected to a sled according to an exemplary embodiment.

Referring to FIG. 7, an exemplary impact tip 700 is shown connected to sled 106. Impact tip 700 includes contact area 708 to be positioned tangent aircraft part 710. Impact tip 700 includes threaded shaft 702 for threaded engagement with sled 106. Nut 704 is threadably engaged with threaded shaft 702 and adjacent sled 106. Nut 704 is self-locking and is used to freeze the position of impact tip 700 relative to sled 106 both horizontally and rotationally. Rotation of nut 704 in a first direction moves nut 704 along threaded shaft 702 away from sled 106 to a loosened position. At the loosened position, rotation of impact tip 700 provides adjustment of the horizontal position of impact tip 700 in direction 712 relative to sled 106 and to aircraft part 710. Once a desired horizontal position is achieved through rotation of impact tip 700 relative to sled 106, rotation of nut 704 in a second direction moves nut 704 along threaded shaft 702 toward sled 106 to a locked position when nut 704 is adjacent sled 106. At the locked position, impact tip 700 cannot be rotated relative to sled 106.

Figure 8:
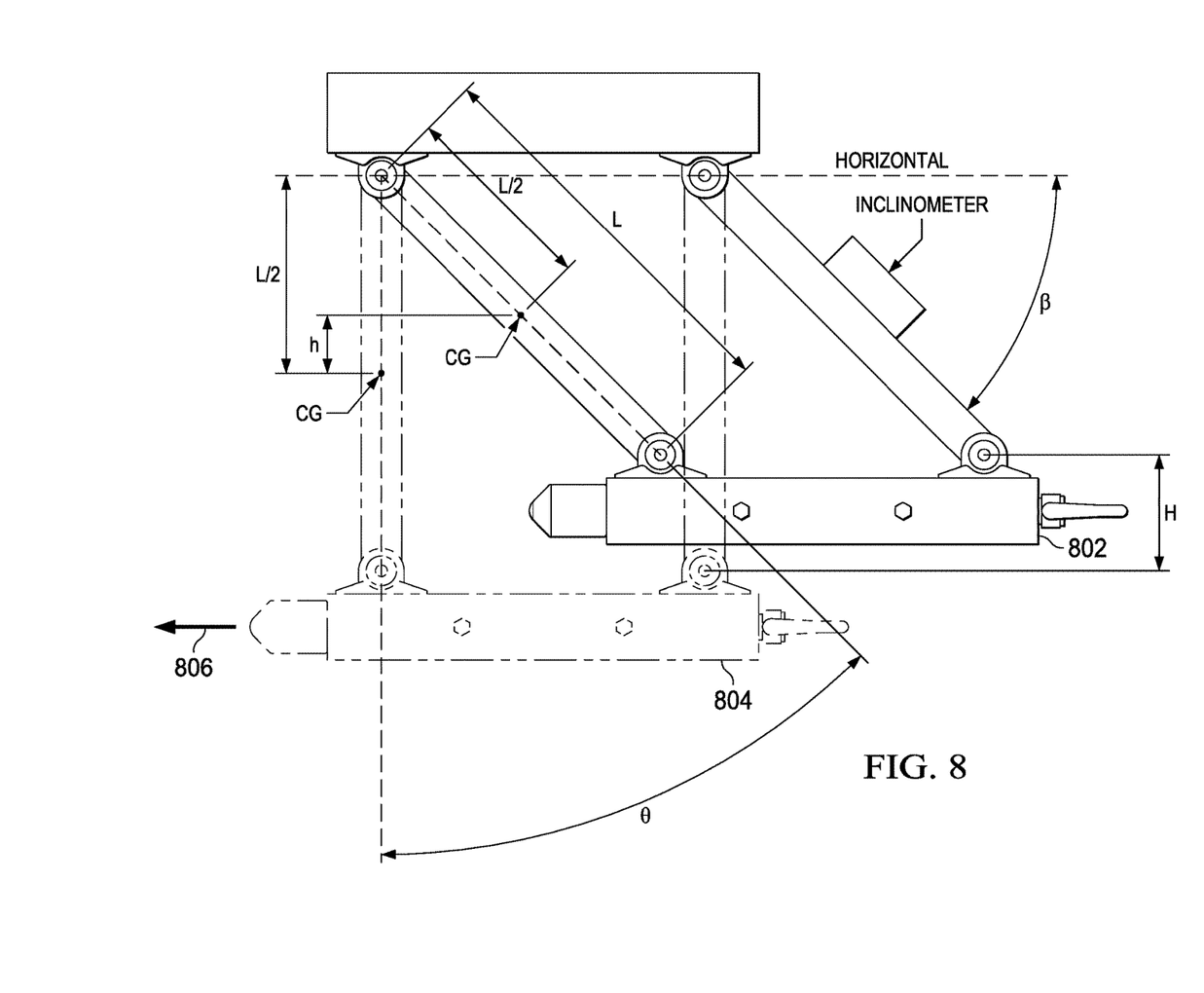
FIG. 8 is a partial side view of a sled in a raised position and an impact position according to an exemplary embodiment.

Referring to FIG. 8, a raised position 802 of the sled and an impact position 804 of the sled are shown. At impact position 804, the impact tip possesses a desired amount of kinetic energy and delivers a force in horizontal direction 806 to a test specimen. The winch attached to the frame and the sled winds the strap up and lifts the sled to raised position 802.

Potential energy of an object is energy an object has because of its position relative to some other object. Potential energy due to gravity (P.E.=mgh) is calculated by multiplying an object's mass (e.g. kilograms) by acceleration due to gravity (9.8 m/s² at the surface of the earth) and by its potential change in height (e.g. meters). Potential energy is typically expressed in Joules where 1 Joule is equal to 1 kg m²/s².

Kinetic energy of an object is energy possessed by an object in motion. The kinetic energy of an object (K.E.=½ mv²) is calculated by multiplying an object's mass (e.g. kilograms) by its velocity squared and dividing by two. Kinetic energy is usually measured in units of Joules.

The kinetic energy of the sled is a result of gravity putting the sled in motion and pulling the sled from the raised position to the impact position. The kinetic energy of the sled at the impact position is equal to the potential energy of the sled at the raised position. Weight of an object accounts for gravity; therefore, the kinetic energy of the sled at the impact position is equal to the weight of the sled times its change in height. The height of the sled is determined by the angle of the links when in the raised position. Since both a desired kinetic energy at the impact position and the weight of the sled are known, the angle of the links from which to release the swinging sled to achieve the desired kinetic energy at the impact position can be found beginning with the following equation:

$$E = WH + 2(wh);$$

where E=the desired impact energy, H=the change in height of the sled, h=the change in height of the center of gravity (CG) of the links, W=the weight of the sled including all bolts, all bearings, any added weights, the hoist ring, and the impact tip, w=the weight of each link, θ=the angle of a link measured from vertical, and β=the angle of a link measured from horizontal. Substituting and simplifying results in the following two equations.

$$\theta = \cos^{-1}(1 - (E/L(W+w)), \text{ and}$$

$$\beta = 90 - \theta$$

An inclinometer verifies when the winch has raised the links to the calculated β and thus the sled has reached raised position 802. Releasing the sled from raised position 802 creates the desired impact energy at impact position 804 where the sled delivers a horizontal force in direction 806.

In use, impact device 100 is positioned proximate a composite aircraft part to which impact damage is desired. Mounting hardware in conjunction with mounting slots 126 removably secure frame 102 to surface such as the floor or a platform. An exemplary impact device 100 may be removably secured to a forklift, movable cart, or other construction as necessary in order to position the device proximate aircraft parts in an installed condition. Impact device 100 is positioned such that the contact area of the impact tip is tangent with the test specimen when links 156 and 158 are parallel with vertical shafts 148 and 150. Rotation of the impact tip adjusts the horizontal position of the impact tip relative to the sled and the test specimen. Rotation of threaded shaft 152 adjusts the vertical position of the impact tip relative to the frame and the test specimen. The winch pulls on the sled such that the links rotate about ball bearings 220, 222, 230, 232, 308, 310, 312, and 314. The sled reaches the raised position when the links reach the calculated angle β. The angle of the links determines the height of the raised position based on the weight of the sled and the amount of impact energy desired to be imparted on the test specimen. Triggering a quick release clasp releases the sled and sets the sled in motion.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an" and other singular terms are intended to include the plural forms thereof unless specifically excluded.

What is claimed is:

1. A mobile impact test machine comprising:
   a frame;
   a set of parallel and coplanar vertical shafts connected to the frame;
   a threaded rod operatively engaged with the frame;
   a carriage, supported by the threaded rod, and slidingly engaged with the set of vertical shafts;
   a first link pivotally engaged with the carriage and pivotally engaged with a sled;
   a second link, parallel with the first link, pivotally engaged with the carriage and pivotally engaged with the sled; and
   an impact tip removably attached to the sled.

2. The mobile impact test machine of claim 1, wherein rotation of the threaded rod adjusts a vertical position of the sled relative to the frame.

3. The mobile impact test machine of claim 1, wherein rotation of the impact tip adjusts a horizontal position of the impact tip relative to the sled.

4. The mobile impact test machine of claim 1, comprising a winch mounted to the frame and releasably connected to the sled.

5. The mobile impact test machine of claim 1, comprising a set of linear sleeve bearings mounted to the carriage and slidingly engaged with the set of vertical shafts.

6. The mobile impact test machine of claim 1, comprising:
   a set of linear sleeve bearings mounted to the carriage and slidingly engaged with the set of vertical shafts;
   a set of clamp-on collars adjacent the set of linear sleeve bearings; and
   wherein when the set of clamp-on collars are engaged, the set of clamp-on collars prevent movement of the carriage relative to the set of vertical shafts.

7. The mobile impact test machine of claim 1, wherein:
   the sled swings relative to the carriage between an impact position and a raised position; and
   the impact tip is configured to contact a test specimen at the impact position.

8. The mobile impact test machine of claim 1, wherein:
   the sled swings relative to the carriage between an impact position and a raised position; and
   the impact tip has a predetermined energy at the impact position.

9. The mobile impact test machine of claim 1, wherein the impact tip has a longitudinal axis and comprises:
   a threaded shaft removably engaged with the sled;
   a body integrally formed with the threaded shaft and defining a contact area;
   a self-locking nut operatively engaged with the threaded shaft and adjacent the sled; and
   wherein rotation of the self-locking nut allows rotation of the body about the longitudinal axis to adjust a horizontal position of the contact area relative to the sled.

10. A method for imparting impact damage to a test specimen using the mobile impact test machine of claim 1, the method comprising:
    positioning the impact tip adjacent the test specimen;
    placing the impact tip at a raised position to achieve a desired impact energy of the impact tip at an impact position adjacent the test specimen;
    releasably securing the impact tip at the raised position;
    releasing the impact tip such that the impact tip pivots about the first and second links to the impact position; and
    impacting the test specimen with the impact tip.

11. The method of claim 10, comprising horizontally adjusting the position of the impact tip relative to the test specimen.

12. The method of claim 10, comprising vertically adjusting the position of the impact tip relative to the test specimen.

13. A repositionable impact test machine for imparting impact damage on a test specimen, the repositionable impact test machine comprising:
    a baseplate connected to a set of beams;
    a canopy connected to the set of beams and vertically aligned with the baseplate;
    a first vertical shaft connected to the baseplate and the canopy;
    a second vertical shaft, parallel and coplanar with the first vertical shaft, connected to the baseplate and the canopy;
    a threaded rod threadably engaged with the canopy;
    a carriage, supported by the threaded rod, and slidingly engaged with the first vertical shaft and the second vertical shaft;
    a first link pivotally engaged with the carriage and pivotally engaged with a sled;
    a second link, parallel with the first link, pivotally engaged with the carriage and pivotally engaged with the sled;
    an impact tip removably attached to the sled;
    wherein the sled moves between a raised position and an impact position; and
    wherein the impact tip comprises a contact area configured to be tangent to a face of the test specimen at the impact position.

14. The repositionable impact test machine of claim 13, wherein the sled is parallel with the carriage.

15. The repositionable impact test machine of claim 13, wherein rotation of the threaded rod adjusts a vertical position of the sled relative to the canopy.

16. The repositionable impact test machine of claim 13, wherein rotation of the impact tip adjusts a horizontal position of the impact tip relative to the sled.

17. The repositionable impact test machine of claim 13, comprising a winch mounted to the canopy and releasably connected to the sled.

18. The repositionable impact test machine of claim 13, comprising:
- a first linear sleeve bearing mounted to the carriage and slidingly engaged with the first vertical shaft;
- a second linear sleeve bearing mounted to the carriage and slidingly engaged with the second vertical shaft;
- a first clamp-on collar adjacent the first linear sleeve;
- a second clamp-on collar adjacent the second linear sleeve; and
- wherein the first clamp-on collar and the second clamp-on collar prevent movement of the carriage relative to the first vertical shaft and the second vertical shaft.

19. The repositionable impact test machine of claim 13, comprising:
- a self-locking nut threadably engaged with the impact tip and adjacent the sled; and
- wherein rotation of the self-locking nut in a first direction allows rotation of the impact tip to adjust a horizontal position of the impact tip relative to the sled; and
- wherein rotation of the self-locking nut in a second direction prevents rotation of the impact tip.

20. The repositionable impact test machine of claim 13, comprising a set of weights removably attached to the sled.

* * * * *